(12) United States Patent
Rowley et al.

(10) Patent No.: US 8,852,290 B2
(45) Date of Patent: Oct. 7, 2014

(54) BIOCOMPATIBLE IMPLANTS AND METHODS OF MAKING AND ATTACHING THE SAME

(75) Inventors: Adrian P. Rowley, Los Angeles, CA (US); Lucien D. Laude, Rabastens-de-Bigorre (FR); Mark S. Humayun, Glendale, CA (US); James D. Weiland, Valencia, CA (US); Atoosa Lotfi, Valencia, CA (US); Francis S. Markland, Jr., Manhattan Beach, CA (US)

(73) Assignee: Doheny Eye Institute, Los Angeles, CA (US)

( * ) Notice: Subject to any disclaimer, the term of this patent is extended or adjusted under 35 U.S.C. 154(b) by 1226 days.

(21) Appl. No.: 12/041,651

(22) Filed: Mar. 3, 2008

(65) Prior Publication Data

US 2008/0306611 A1    Dec. 11, 2008

Related U.S. Application Data

(60) Provisional application No. 60/904,919, filed on Mar. 2, 2007.

(51) Int. Cl.
| | | |
|---|---|---|
| A61F 2/02 | (2006.01) | |
| A61L 27/34 | (2006.01) | |
| A61L 27/50 | (2006.01) | |
| A61N 1/05 | (2006.01) | |
| A61N 1/36 | (2006.01) | |
| A61F 2/14 | (2006.01) | |

(52) U.S. Cl.
CPC ........... *A61N 1/0543* (2013.01); *A61N 1/36046* (2013.01); *A61L 27/34* (2013.01); *A61L 2400/18* (2013.01); *A61F 2/14* (2013.01); *A61L 27/50* (2013.01)
USPC ...... 623/23.74; 623/4.1; 204/157.15

(58) Field of Classification Search
USPC .......... 424/422; 623/1.11, 23.72, 4.1, 623/5.11–5.16, 6.11–6.64; 427/2.24; 524/588; 428/318.4; 264/482; 204/157.15
See application file for complete search history.

(56) References Cited

U.S. PATENT DOCUMENTS

| | | | |
|---|---|---|---|
| 4,346,330 A | 8/1982 | Lee et al. | |
| 4,969,912 A * | 11/1990 | Kelman et al. | 128/898 |

(Continued)

FOREIGN PATENT DOCUMENTS

WO    WO 2005/110469 A2    11/2005

OTHER PUBLICATIONS

Mao et al., "Laser ablation processes investigated using inductively coupled plasma-atomic emission spectroscopy (ICP-AES)", Applied Surface Science 127-129, (1998) pp. 262-268, Elsevier Science.

*Primary Examiner* — Mark Mashack
(74) *Attorney, Agent, or Firm* — James W. Hill; Nathan S. Smith; McDermott Will & Emery LLP

(57) ABSTRACT

The invention provides a biocompatible silicone implant that can be securely affixed to living tissue through interaction with integral membrane proteins (integrins). A silicone article containing a laser-activated surface is utilized to make the implant. One example is an implantable prosthesis to treat blindness caused by outer retinal degenerative diseases. The device bypasses damaged photoreceptors and electrically stimulates the undamaged neurons of the retina. Electrical stimulation is achieved using a silicone microelectrode array (MEA). A safe, protein adhesive is used in attaching the MEA to the retinal surface and assist in alleviating focal pressure effects. Methods of making and attaching such implants are also provided.

26 Claims, 12 Drawing Sheets

POLYMERIC SiO   OR   p-SiO* o  OXYGEN
⊘  SILICON
⇨  "DANGLING BOND" ELECTRON ORBITAL

RGD SEGMENTS OF PROTEINS
INTERACT WITH INTEGRINS

(56) References Cited

U.S. PATENT DOCUMENTS

| | | | |
|---|---|---|---|
| 5,177,165 A | 1/1993 | Valint, Jr. et al. | |
| 5,531,857 A * | 7/1996 | Engelsberg et al. | 156/345.5 |
| 5,713,957 A * | 2/1998 | Steele et al. | 623/5.16 |
| 6,280,760 B1 * | 8/2001 | Meyer et al. | 424/423 |
| 6,324,429 B1 * | 11/2001 | Shire et al. | 607/54 |
| 6,710,030 B1 * | 3/2004 | Markland et al. | 514/21.2 |
| 7,163,730 B2 | 1/2007 | Dhaler et al. | |
| 2003/0078658 A1 * | 4/2003 | Zadno-Azizi | 623/6.37 |
| 2004/0248429 A1 | 12/2004 | Aoki | |
| 2005/0191847 A1 | 9/2005 | Misawa et al. | |
| 2006/0051522 A1 | 3/2006 | Talton | |
| 2006/0111005 A1 | 5/2006 | Geohegan et al. | |
| 2006/0204738 A1 | 9/2006 | Dubrow et al. | |
| 2006/0251795 A1 | 11/2006 | Kobrin et al. | |
| 2007/0179086 A1 | 8/2007 | Gliniak et al. | |

\* cited by examiner

POLYMERIC SiO   OR   p-SiO*

○ OXYGEN
⊘ SILICON
⬯ "DANGLING BOND" ELECTRON ORBITAL

BIOCOMPATIBLE IMPLANTS AND METHODS OF MAKING AND ATTACHING THE SAME

CROSS-REFERENCE TO RELATED APPLICATIONS

This application is based on and claims the benefit of U.S. provisional application No. 60/904,919, filed Mar. 2, 2007, the entire contents of which are incorporated by reference herein.

STATEMENT REGARDING FEDERALLY SPONSORED RESEARCH OR DEVELOPMENT

This application was made with government support under Grant Nos. DOE-(Artificial Retina program) and NSF-EEC-0310723 (BMES ERC), awarded by The United States Department Of Energy and the National Science Foundation, respectively. The government has certain rights in the invention.

BACKGROUND OF THE INVENTION

Silicones are polymeric materials that have one characteristic in common: the polymer backbone is made of an alternate succession of Si and O atoms, joined together via strong, covalent inter-atomic bonds. The Si atoms are coupled to two adjacent O atoms and two organic radicals, i.e., C—H or C—R, where R is an organic group or moiety. The various silicones only differ from each other via these organic radicals, e.g. methyl (—$CH_3$), vinyl (—HC=$CH_2$), or other organic functional group. Silicones are variously referred to as "polymerized siloxanes," "polysiloxanes," and "silicone polymers." "Silicone rubbers" are included in this definition but typically include one or more additives, such as fillers, plasticizers, and crosslinkers. We use the term "silicone" in its broader sense to refer to silicone polymers, whether or not modified with one or more additional components.

Silicones are notably neutral to the environment, asserting in particular no chemical interaction with foreign molecules. They also exhibit very low electrical conductivity and are fully transparent to visible or infra-red light. They absorb light photons in the UV range, typically at and below 280 nm wavelength (i.e. at and above 4.4 eV photon energy).

In order to allow chemical coupling of silicone materials to foreign species, it is necessary to "open" their structure, i.e. to modify irreversibly their atom assembly via breaking irreversibly some of the inter-atomic bonds. Unfortunately, this may not be accessible to mechanical action. In effect, given that these materials are elastic, they may change considerably their configuration through pulling without breaking bonds, this being in particular a consequence of the rotational symmetry of the Si—O bonds. Similarly, opening the silicone structure may not be feasible via thermal means. Silicone does not melt, sublimate or evaporate but rather condenses and transforms in a glassy and extremely fragile network at temperatures exceeding 230° C.

Due to their chemical inertness, silicones are recognized as biocompatible materials and are widely used in practical medical implants. For example, an epiretinal visual prosthesis (a microelectrode array (MEA) imbedded into or onto a silicone substrate, or applied using photolithography) is a device that can be implanted on the retina and converts images into electrical signals that stimulate the retina. The images are received from an external camera and transfer the visual information to the MEA.

Unlike cells, which attach to their extracellular environment via integral membrane proteins called integrins, MEAs and other medical implants are generally affixed to adjacent tissue using surgical tacks or adhesives, which may be actually or potentially harmful to the tissue and, therefore, may limit the actual lifetime of the implant function. For example, a method currently used to fix an epiretinal visual prosthesis in place utilizes surgical tacks secured to the retina, which cause local pressure effects, local tissue destruction, and vascular leakage. Pressure is a crucial component of the cellular environment and can lead to pathology if it varies beyond the normal range. Disorders of this relationship can lead to disease states, such as glaucoma, in which retinal ganglion cells undergo apoptosis and necrosis.

A major obstacle faced by bioengineers has been the ability to attach proteins to biocompatible substrates, and there is a continuing need for biocompatible materials and less destructive methods of attaching them to tissues. If silicone implants are to be fixed in place in the body, a way must be found to "activate" the silicone polymers to permit them to bond more readily to one or more compounds, such as cellular or extracellular proteins.

SUMMARY OF THE INVENTION

The present invention provides a new generation of biomaterials capable of interfacing with human or other living tissue; a method of making implants and other articles made of such materials, and a method of affixing a biocompatible medical implant to living tissue. In a first aspect of the invention, a silicone article treated with a biocompatible compound that facilitates bonding to living tissue comprises a silicone substrate having at least one activated surface formed by irradiation with laser light at a wavelength and power sufficient to eject organic species from the silicone substrate, and at least one compound (e.g., an RGD peptide or protein) capable of binding to one or more integrins, coupled to the activated surface. In one embodiment, the silicone article is a biocompatible, implantable prosthesis comprising a prosthesis partially or completely covered with a silicone having at least one activated surface; and at least one biocompatible compound capable of binding to one or more integrins, coupled to said at least one activated surface. A specific example is a microelectrode array for an epiretinal visual prosthesis. (FIG. 1).

In a second aspect, the invention provides a method of making a biocompatible, implantable prosthesis, comprising the steps of providing an implantable prosthesis; partially or completely covering the implantable prosthesis with a silicone having at least one activated surface; and coupling at least one biocompatible compound capable of binding to one or more integrins to said at least one activated surface.

In a third aspect, the invention provides a method of securing an implantable prosthesis to living tissue, comprising the steps of providing an implantable prosthesis partially or completely covered by a silicone having at least one activated surface, the activated surface being coupled to at least one biocompatible compound capable of binding to one or more integrins; and allowing the at least one compound to interact with cellular membrane proteins in the tissue, thereby securing the implantable prosthesis to the tissue.

As used herein, the term "silicone article" means a physical item that contains, as a major component, one or more silicone polymers. Other components, such as fillers, crosslinkers, plasticizers, other polymers, etc., may also be present The article can be a self-supporting object, such as a film, protective sleeve or jacket, component of a larger assembly, etc., or a coating on another object. The term "activated surface" is described below in detail.

The invention offers essential advantages over current practice and may be applied to any type of silicone-containing implant. In particular, it shows how a specific laser-activated silicone surface may be utilized in strongly fixing an implant on a living tissue without interfering with (i) that tissue, and (ii) the function of the implant.

BRIEF DESCRIPTION OF THE DRAWINGS

Various features and embodiments of the invention will become more clear when reference is made to the appended drawings, wherein.

DETAILED DESCRIPTION OF THE INVENTION

In a first aspect of the invention, a silicone article treated with a biocompatible compound is provided, and comprises a silicone substrate having at least one activated surface formed by irradiation with laser light at a wavelength and power sufficient to eject organic species from the silicone substrate, and at least one compound capable of binding to one or more integrins, coupled to the activated surface. In one embodiment, the silicone article comprises or is part of an implantable medical device or prosthesis, as described below.

Nonlimiting examples of silicone articles include silicone films, substrates, bulk objects, and silicone coatings. The silicone may be present as substantially pure silicone polymers or, more typically, silicone polymers containing one or more additives to enhance the article's mechanical, thermal, or other physical characteristics. Nonlimiting examples of such additives include fillers, such as silica entities (e.g., foamed, granular, fibrous, etc; optionally, the silicone polymers are coupled to these silica entities via grafting), plasticizers, and crosslinkers, which can be admixed with the silicone-silica compounds to ensure lateral coupling between polymeric chains that are attached (i.e. grafted) to the same silica piece; etc. The whole of a silicone/silica/crosslinker assembly constitutes a silicone rubber. Varying any of the individual constituents in quality and quantity provides a nearly infinite range of silicone rubbers that can be activated according to the invention.

Integrins are integral membrane proteins used by cells to attach to their extracellular environment. Treating an activated silicone surface with a compound capable of binding to one or more integrins makes it possible to attach a silicone article, such as an implant, directly to tissue, without resort to surgical tacks, toxic adhesives, or other potentially destructive means.

Figure 6:
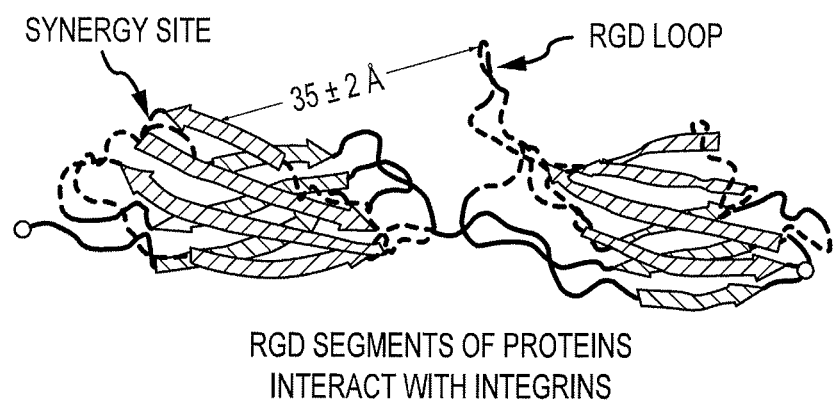
FIG. 6 is a schematic drawing showing the interaction of RGD segments of proteins with integrins, according to one embodiment of the invention.
Figure 7:
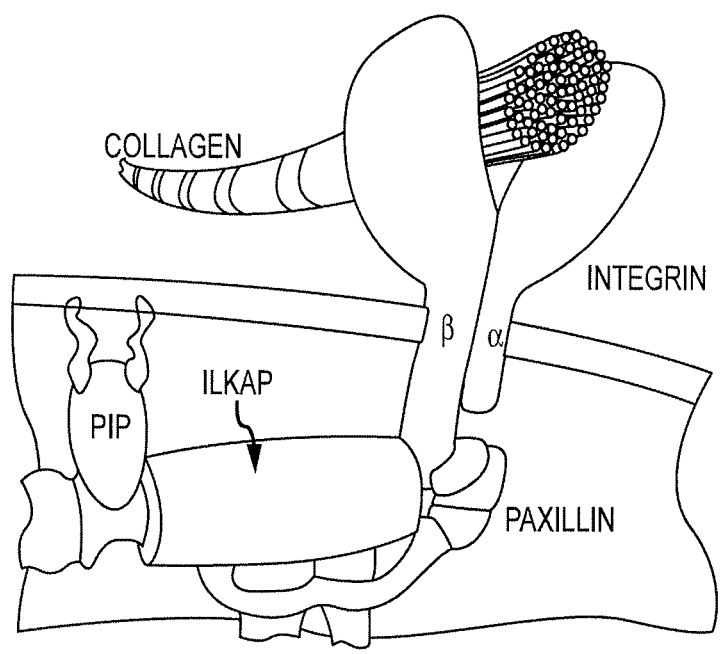
FIG. 7 is a schematic drawing showing how proteins bind integrins via an RGD segment, according to one embodiment of the invention.

One type of compound capable of binding to integrins is an arginine-glycine-aspartate (RGD) peptide, or a protein containing at least one RGD segment (FIG. 6). Extracellular matrix (ECM) proteins can be used to bind integrins via RGD segments at the cellular interface (FIG. 7). Nonlimiting examples include fibronectin, laminin, and collagen. Non-ECM proteins that contain one or more RGD segments are another example of compounds capable of binding to integrins; specific examples include Contortrostatin (CN), a low molecular weight protein found in snake venom, and Vicrostatin, the monomer of CN. Both of these two proteins stick to integrins on tissue previously occupied by ECM proteins. CN works well (i.e., it is sticky) as it is small and has two RGDs per molecule. Extracellular matrix proteins (such as fibronectin, laminin and collagen) do not adhere as well to the retina as they are large molecules with only one RGD; however they do adhere well to the activated silicone.

To prepare a silicone substrate having at least one activated surface, laser light of sufficient wavelength and power is directed at one or more surfaces of a silicone article, such as the top of a silicone film, a portion of a surface of a silicone prosthesis, etc., which causes chemical bond breaking and formation of unpaired electrons, as described below. This "activates" the surface of the silicone article in and around the areas that have been irradiated, making that area more chemically reactive toward other compounds.

The use of a monochromatic, intense UV light source can, under specific conditions, allow substantially instant light absorption and drive the silicone structure to destabilize its atom configuration. This can be achieved with a laser source working in the UV range and under a pulsed regime, such as an excimer laser.

After investigating the actual optical absorption of a given silicone or silicone rubber, a UV light wavelength (or photon energy) is chosen that allows the material to absorb the UV photons selectively and exclusively on the Si—C bond electrons. Above a given power of the light source at that wavelength (of the order of 100 MW), all Si—C bond electrons that are present in the silicone volume that is traversed by the laser beam may be brought to absorb these UV photons quasi-simultaneously, over a very short period of time (on the order of 1-2 ns). That absorption produces the quasi-simultaneous breaking of these Si—C bonds, thus separating the corresponding organic species, e.g., organic radicals from the original silicone structure. While these radicals form a gas that disperses in the environment, the Si—O backbones of the now partially decomposed polymer remain as the sole part of the silicone that has not absorbed the UV photons. Meanwhile, each of the Si atoms in the polymer backbones is no longer fully interlinked except to two adjacent O atoms. This leaves two unpaired electrons per Si atom. Each of these electrons remains coupled to a corresponding positron in the atom nucleus and occupies a so-called orbital that is attached to the atom site. After laser irradiation of the original surface, these "dangling" bond electron orbitals constitute a dense one-dimensional network along each backbone on the actual silicone surface.

That network materializes the chemical "activation" of the processed silicone surface. In effect, and as a result of the laser-processing, the surface is no longer neutral, but is negatively charged. Eventually, an electric field is established that stems from these orbitals and tends to attract (i) positively charged species to form covalent bonding, or even (ii) neutral species that come to settle on the silicone surface and adhere to the Si—O backbones via electrostatic forces.

The end product of the laser-processed silicone surface is partially ablated and, therefore, engraved (i.e. recessed) down to some 10 μm or more below the original surface plane, depending on the number of super-imposed irradiations. The activated surface is, therefore, originally localized in the recessed area but is not limited to it, as explained by the discussion.

As noted above, C—H or other organic radicals are liberated during irradiation as free entities. The cloud of chemical species that is formed by these radicals tends to project outwards nanometer-scale particles (or nano-particles) of the silicone (Si—O) backbones. These nano-particles land on and populate the silicone surface area that is adjacent to the recessed laser-irradiated parts, thus contributing to the formation of a laser-activated silicone surface. Over that area, they form a dense layer of active species, since they contain those unpaired dangling bond electrons on each Si atom as mentioned above. Eventually, these species do react to the underlying virgin silicone surface, resulting in a strongly adherent, active cover. As a result, activation of the silicone surface is no longer restricted to the recessed laser-processed surface but extends eventually far beyond it.

This extended activation is conformal to the un-recessed, original silicone surface. The geometry of the conformal activated surface that surrounds the laser-recessed parts may be tailored through the actual geometry and distribution of these laser-processed recessed areas. Since the latter may be monitored by precisely positioning and/or scanning the laser beam onto the silicone surface, the entire conformal activated surface may be designed through computer-monitoring of the laser positioning on the silicone surface.

All silicones (including silicone rubbers) are accessible to the above-described laser-induced selective decomposition and activation. Such materials may differ by the type of organic-radicals that they contain. However, because each radical is connected to a single Si atom by a normal Si—C bond, different organic-radicals may be identically separated from their silicone backbone via identical irradiation conditions, irrespective of the individual identity of the organic-radicals and silicone formulation.

Three types of bonds are present in every silicone: Si—O, Si—C and C—H. The weakest of these bonds is Si—C (at 318 kJ/mol), the strongest is Si—O (at 452 kJ/mol), and C—H is intermediate in strength at 411 kJ/mol. Along with that bond hierarchy, optical absorption starts at 4.3, 5.3, and 5.5 eV, for Si—C, C—H, and Si—O bond (valence) electrons, respectively. Choosing a monochromatic beam working at 5 eV photon energy (i.e., 248 nm wavelength) restricts exclusively optical absorption to electrons belonging to Si—C bonds.

Increasing the actual power of a laser beam working at 5 eV should therefore allow the selective decomposition of silicone that preserves the original Si—O backbone and produces the formation of the dangling bond electrons that materialize the activation of the material. Comparatively, such 5 eV photons are not absorbed by silica additive parts. In contrast, they may be absorbed by crosslinker molecules, whether these are a silicone polymer or siloxane. In that case, again C—H and other organic radicals are selectively separated from the backbone of these molecules, without affecting their inter-linking function.

The preferred laser source that promotes this selective optical absorption to the most appropriate power is an excimer laser source working at 248 nm wavelength, i.e. 5.00 eV photon energy. Its actual instant power (i.e. beam energy/pulse duration) may vary in the range of 50 to 200 MW. Alternatively, another laser source is utilized, though not necessarily with the same effectiveness. For example, a pulsed, quadrupled-YAG laser beam would likely operate less efficiently.

In one embodiment, the irradiation is pulsed (pulse duration being variable in the range 5 to 40 ns, full width, depending on manufacturer). Pulses are usually repeated several times along a train, at fixed time intervals. The processed material may be maintained fixed during irradiation, and the train of pulses processes the same area until a specific amount of ablated (activated) matter is produced. While being irradiated (i.e. during laser-scanning), the target polymeric material may also be displaced in front of the laser source on an X-Y table, moving perpendicularly to the laser beam axis. An appropriate combination of pulse repetition rate and scan velocity would ensure the required ablation per unit area. Material displacement is computer-controlled to any geometry and scan-speed velocity.

The ablated species scatter around the laser-ablated area and establish the laser-activated silicone surface. Optionally, the extent of the scatter may either be limited to a few μm or expanded to several hundred μm, using a gas jet (e.g., an inert gas, such as He) that drifts the emitted species away from the irradiated area, and the scan geometry can be adapted to account for that scatter. In contrast, a monochromatic beam working at a photon energy exceeding 5.5 eV induces absorption from all valence electrons, irrespective of the bond type from which they originate. At and above an appropriate instant power level, this would eventually drive the full ablation of silicone with no activation of the remaining silicone surface, either of the irradiated part of it or of the surface area surrounding it.

Excimer lasers have been used to irradiate plastics to form metallized plastics. See U.S. Pat. No. 5,599,592 to L. Laude, entitled "Process For The Metallization of Plastic Materials and Products Thereto Obtained," the entire contents of which are hereby incorporated by reference.

Figure 1:
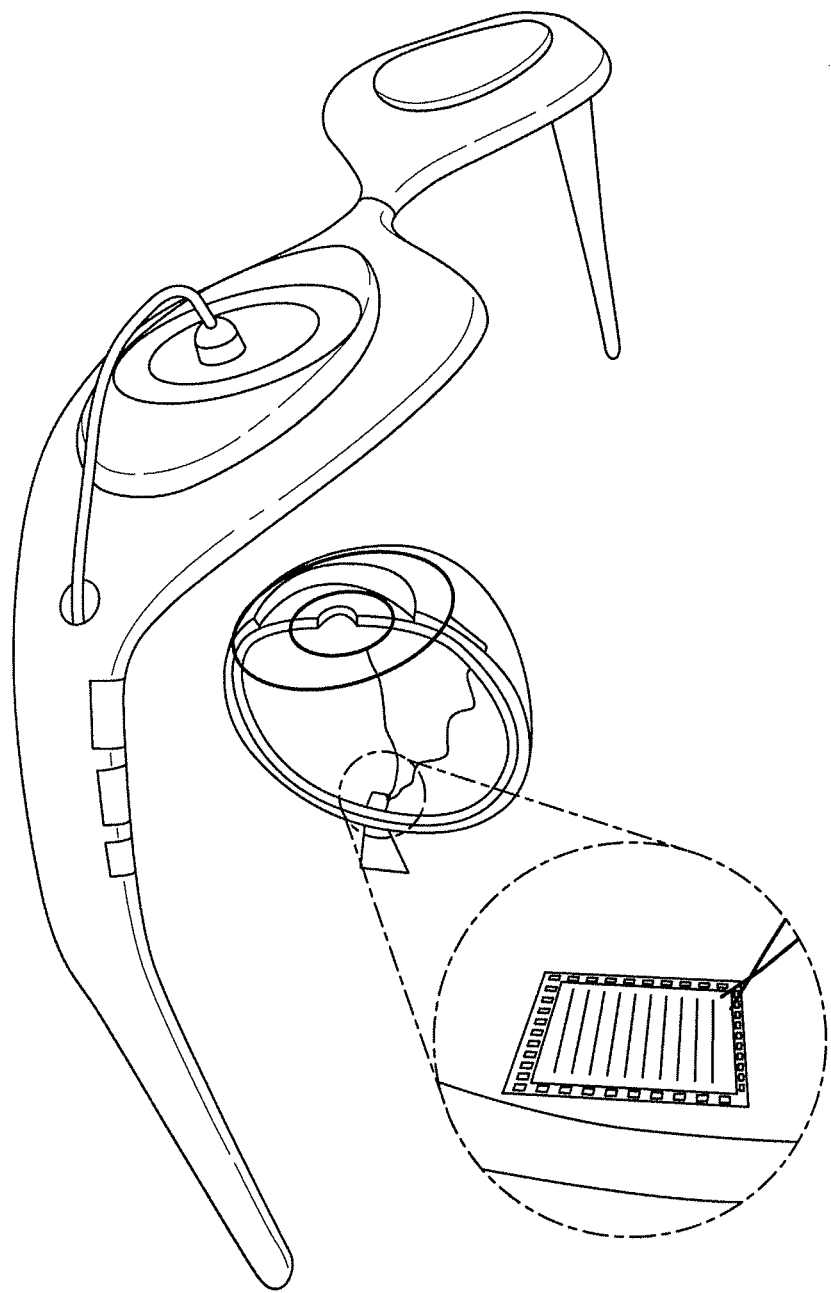
FIG. 1 is a schematic illustration of an MEA implanted on a retina in communication with spectacles containing an external camera.
Figure 2:
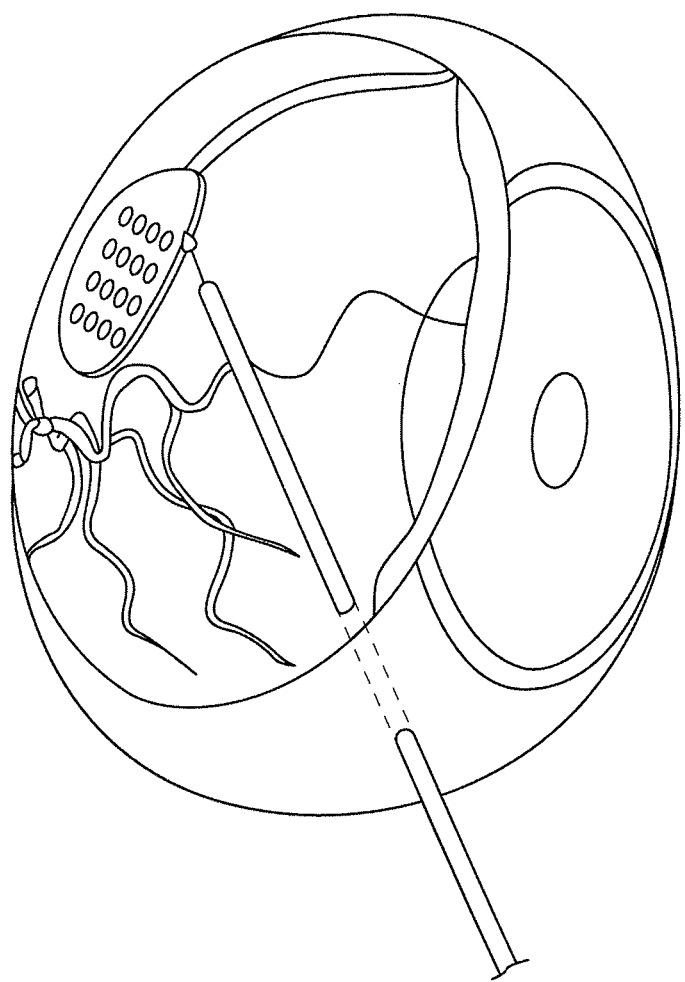
FIG. 2 is a schematic illustration of the prior art tacking of an MEA to the retina.
Figure 3:
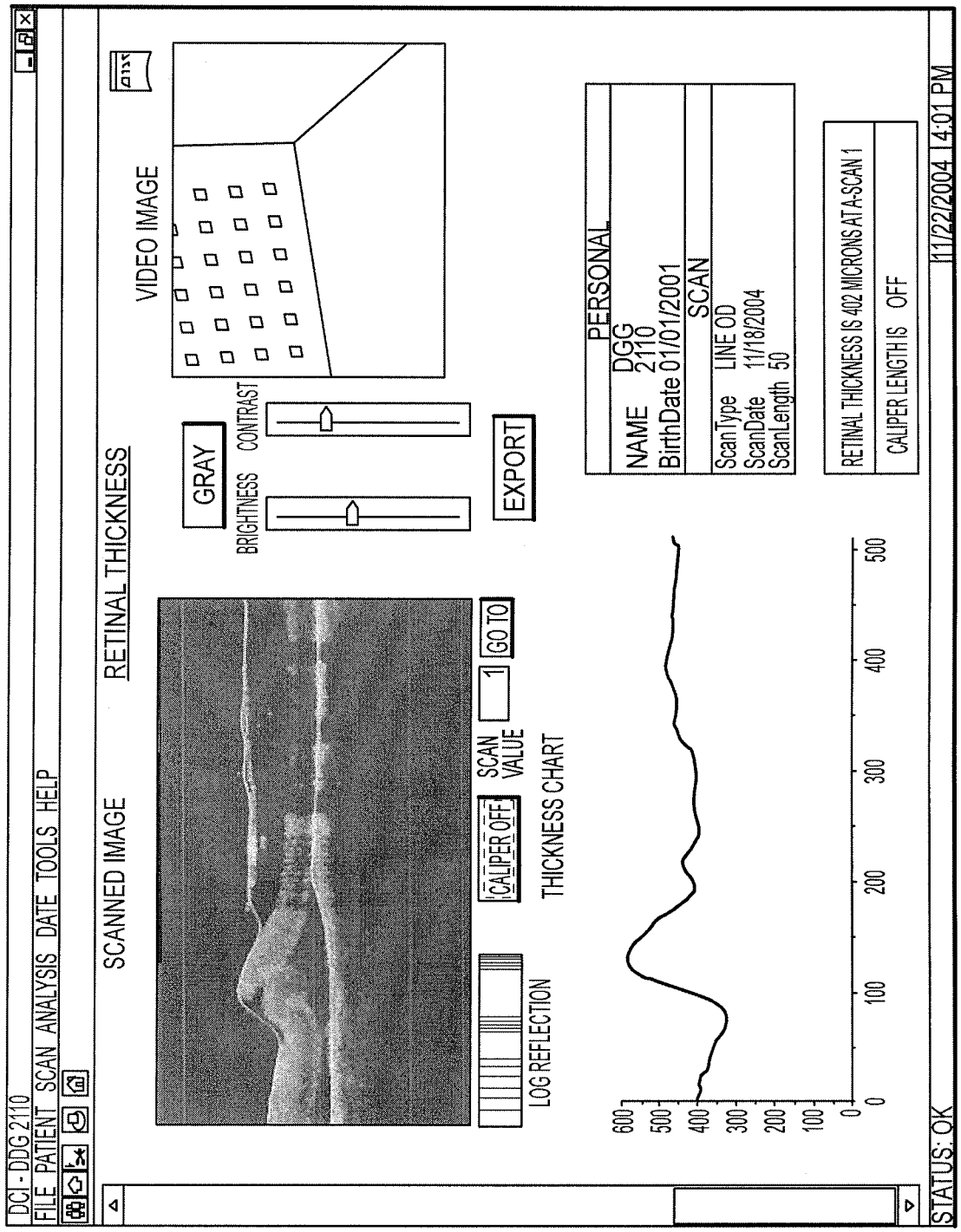
FIG. 3 is a prior art screenshot showing the optical coherence tomography (OTC) of a retinal fold.
Figure 4:
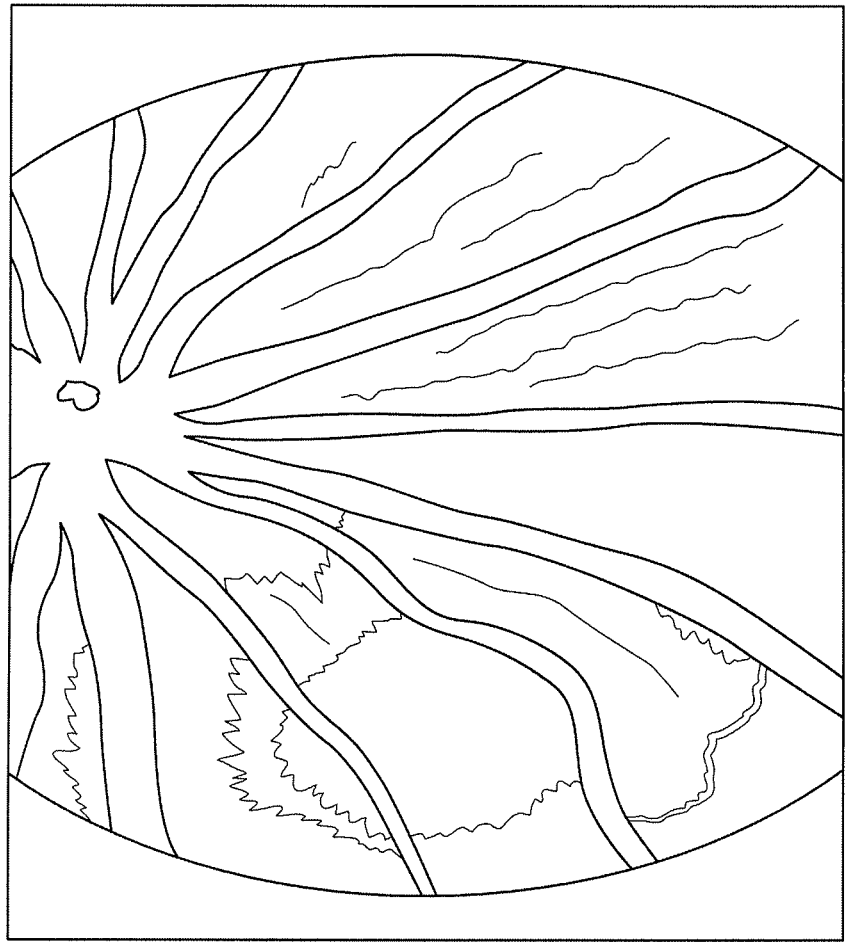
FIG. 4 is a prior art photograph showing vascular leakage due to focal pressure in a rat.
Figure 5:
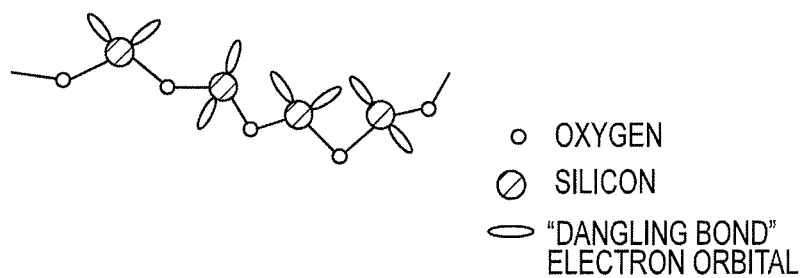
FIG. 5 is a schematic drawing of polymeric SiO, created by laser activation according to one embodiment of the invention.

FIG. 5 schematically depicts a conceptualization of a laser-activated silicone surface according to the invention. As shown, chemically reactive, dangling unpaired electrons bound to the Si—O backbone are exposed at the surface. The surface is thus "activated," and can react with other compounds of interest.

In one embodiment, a silicone article having at least one activated surface formed by irradiation with laser light at a wavelength and power sufficient to eject organic species from the silicone article is prepared according to the method described above. In addition, the article further comprises one or more compounds capable of binding or adhering to one or more integrins, as described above. A convenient way to apply the compound(s) to the activated surface is to provide it as a gas or liquid, the latter being particularly suited for introducing large molecular structures, such as peptides and proteins that are otherwise difficult to manipulate. If these are contained in a liquid solution, coating may be done by hand (e.g.,), disposing a drop of the solution on the irradiated surface(s) of the silicone article.

Advantageously, coupling of the compound(s) to the silicone surface is generally restricted to the laser-activated areas as described above. When these structures are contained in a liquid solution, a drop of that solution may be disposed (e.g., manually) on the silicone surface. Only the parts of the surface that have been activated would retain the incoming species and ensure substantial adhesion and bonding. On non-activated surface areas, foreign species do not adhere to the virgin silicone surface and may, therefore, be removed by washing in water, gentle scrubbing, or tapping out without affecting those species that are strongly fixed on the activated silicone surface. Other means of disposing these foreign species may be practiced depending on the type and size of the species. For example, disposal may also be performed by evaporation in a vacuum chamber, and other physical or chemical means may be practiced as well without affecting the particular adhesion of these species to the laser-activated silicone surface alone.

The type and extremely dense distribution of the laser-generated activated parts of the silicone polymer (namely, the Si—O backbones) on a laser-processed silicone surface allow the surface to size, and keep at once, large molecules of varied formulation and shape. This is demonstrated, for example, in disposing protein molecular structures onto an activated silicone surface.

One type of silicone article that can be prepared according to the invention is a silicone implant, i.e., an implantable medical device made, in whole or in part, of silicone. (In other words, silicone may constitute substantially the entire implant, or just a part of it, such as an outer coating, sleeve, jacket, or other protective barrier.) In one embodiment, the silicone implant is a silicone article treated with a biocompatible compound that facilitates bonding to living tissue, and comprises a silicone substrate having at least one activated surface formed by irradiation with laser light at a wavelength and power sufficient to eject organic species from the silicone substrate, and at least one compound capable of binding to one or more integrins, coupled to the activated surface.

Because retinal cells can bind to RGD peptides and proteins containing RGD segments, the present invention can be used to make an epiretinal visual prosthesis—a silicone-coated microelectrode array (MEA) to be implanted in the eye. The internal limiting membrane of the retina (the innermost layer) contains laminin, fibronectin, collagen type I and IV, protecglyeans and vitreous fibrils.

Biocompatibility of an epiretinal positioned electrode array is an important consideration when choosing the materials for the MEA. Additionally, the surgical techniques also play a role in the success of the implanted array. See *Long-term Histological and Electrophysiological Results of an Inactive Epiretinal Electrode Array Implantation in Dogs, Invest. Opthalmol. Vis. Sci.*, vol. 40, no. 9, pp. 2073-2081, August 1999 by A. B. Majji, the entire contents of which are hereby incorporated by reference.

Techniques for attaching arrays to ocular tissue using biological glues, retinal tacks, and magnets are known in the art. See *Bioadhesives for Intraocular Use, Retina*, vol. 20, pp. 469-477, 2000, by E. Margalit et al., the entire contents of which are hereby incorporated by reference. Fabricating silicone microelectrode arrays is also known in the art. See *Retinal Prosthesis for the Blind, Surv. Opthalmology*, 47 (2002), pages 335-356 by E. Margalit, et al., the contents of which are hereby incorporated by reference. See also, U.S. Department of Energy document UCRL-LR-153347, entitled *Microfabrication of an Implantable Silicone Microelectrode Array for and Epiretinal Prosthesis* by M. N. Maghribi, dated Jun. 10, 2003; *Batch-fabricated thin-film Electrodes for Stimulation of the Central Auditory System, IEEE Trans. Biomed. Eng.*, vol. 36, o. 7, pp. 693-704, July 1989 by D. J. Anderson, et al.; *An Integrated-circuit Approach to Extracellular Microelectrodes, IEEE Trans. Biomed. Eng.*, vol. BME-17, pp. 238-247, 1970 by K. D. Wise et al.; *Implantable Microsystems. Polyimide-based Neuroprostheses for Interfacing Nerves, Med. Device Tech.*, vol. 10, no. 6, pp. 28-30, July 1999, by T. Stieglitz et al.; the entire contents (of all of the prior references) of which are hereby incorporated by reference.

In one embodiment, implanted components can include a multi-channel electrode array as well as bi-directional telemetry and hermetically packaged micro-electronics. These components can perform power recovery, management of data reception and transmission, digital processing, and analog output of stimulus current.

In one embodiment, for a silicone implant comprising a microelectrode array (MEA), and if an extracellular matrix (ECM) protein is selected as the compound coupled to the activated silicone surface, it is advantageous if the ECM protein has at least one of the following characteristics: (i) an RGD (arginine-glycine-aspartate) amino acid segment to enable it to interact with retinal integrins (see FIGS. 6 and 7), (ii) disulfide bonds to allow covalent interaction with silicone, (iii) enzyme-cleavable regions to facilitate removal of the MEA.

A non-limiting list of polymers useful for creating flexible, micro-electrode arrays are silicone, polyimide, polydimethylsiloxane, and parylenes, such as parylene N and C, and copolymer blends of silicone and non-silicone polymers. Note that non-silicones like the polyimides and parylenes, without being combined with a silicone based polymer, may not have activated surfaces when subjected to the excimer laser process, but are still useful polymers for retinal implants.

In one embodiment, the activated silicone may be used for long or short-term medical devices such as implants and drug delivery devices, and in a number of tissues, including brain (e.g., cortex), heart, liver, and eye (e.g., retina). A non-limiting list of medical devices includes cardiac pacemakers, cochlear implants, deep brain stimulators for Parkinson's disease, and epiretinal visual prostheses. For these devices, establishing good contact with the surrounding tissue is important and thus the attachment methods of the present invention may be used. The use and implanting of cochlear implants is known in the art. See *Cochlear Prosthetics, Ann. Rev. Neurosci.*, vol 13, pp. 357-371, 1990, by G. E. Loeb, the entire contents of which are hereby incorporated by reference. Using implants to treat Parkinsonian tremors is also known in the art. See *High-frequency Unilateral Thalmic Stimulation in the Treatment of Essential and Parkinsonian Tremor, Ann. Neurol.*, vol. 42, no. 3, pp. 292-299, September 1997, the entire contents of which are hereby incorporated by reference.

From the foregoing discussion it can be appreciated that the invention also provides a method of making a biocompatible, implantable prosthesis, comprising the steps of providing an implantable prosthesis; partially or completely covering the prosthesis with a silicone having at least one activated surface; and coupling at least one biocompatible compound capable of binding to one or more integrins to the activated surface. In addition, the invention provides a method of securing an implantable prosthesis to living tissue, the method comprising the steps of providing an implantable prosthesis partially or completely covered by a silicone having at least one activated surface, the activated surface being coupled to at least one biocompatible compound capable of binding to one or more integrins; and allowing the at least one compound to interact with cellular membrane proteins in the tissue, thereby securing the implantable prosthesis to the tissue.

If it becomes necessary to remove such an implant from tissue to which it has been attached, an enzyme such as plasmin can be used cleave RGD peptides, thereby breaking the bond between the implant and adjacent integrins.

Examples, Tests, and Discussion

Protein Attachment to a Silicone Surface

Snake venom disintegrin (Contortrostatin) is a homodimeric protein that contains an RGD amino acid segment and disulfide bonds that allow the protein to attach to activated silicone. An excimer laser was used to physically break the molecular bonds and produce dangling free bonds on the silicone surface. Using a pipette, the Contortrostatin was dropped onto the lased silicone surface and allowed to dry.

Preparation of Retinal Tissues

Postmortem porcine eyes were prepared by removing the vitreous humor with a vitreous cutter (Bausch and Lomb). The posterior segment of the eye was flattened by making four cuts in four different quadrants from the pars plana to the equator. The eye was pinned out onto a polystyrene surface and quadrants of the retina were delicately removed. Each piece of retina was glued (Adhesive Systems RP 1500 USP) face up (i.e. internal limiting membrane up) to a piece of aluminum and allowed to dry for 10 minutes. During this time the retina was kept moist with drops of saline.

Protein Adhesive Strength

The adherence forces between the Contortrostatin-coated silicone and the retina were measured by dynamic mechanical analysis, using a Bose ElectroForce 3100. Contortrostatin-coated silicone was glued (Adhesive Systems RP 1500 USP) to a piece of plastic and lowered onto the prepared retina. The silicone piece was raised 4 mm over 10 seconds and the adhesive forces resulting from the separation of retina and aluminum were recorded.

Results

Figure 8:
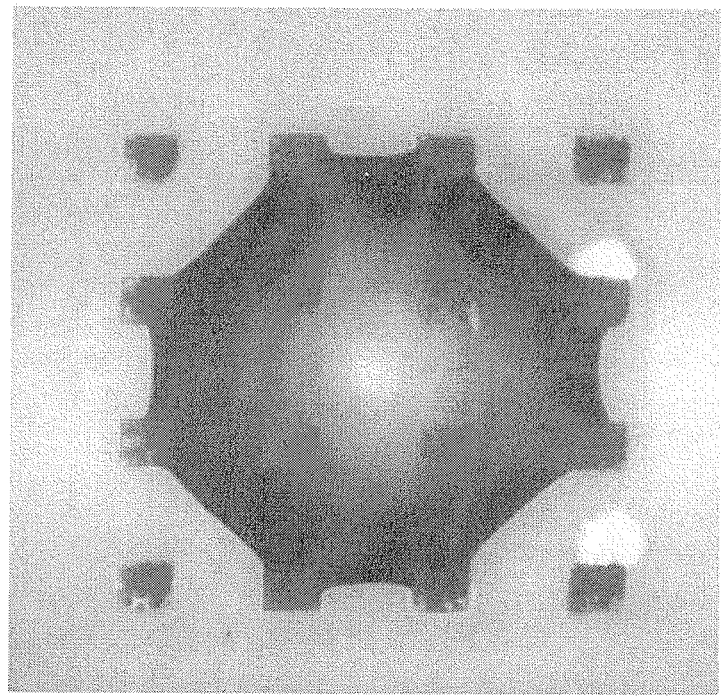
FIG. 8 is a photograph of a Contortrostatin drop on a laser-activated surface according to one embodiment of the invention.
Figure 9:
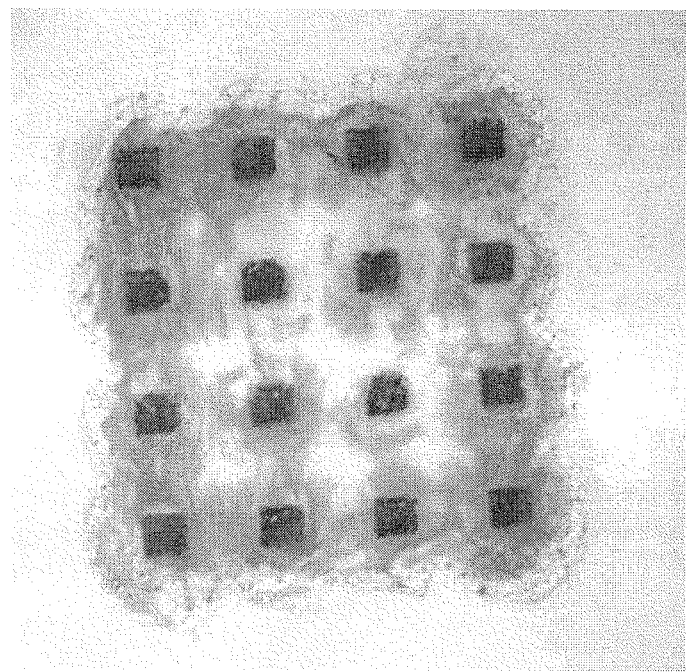
FIG. 9 is a photograph illustrating how Contortrostatin adheres to silicone debris according to one embodiment of the invention.

After the excimer laser was used to physically break molecular bonds, photos were taken of the silicone surface during the attachment process. The Contortrostatin drop can be seen absorbing into the lased areas (FIG. 8) and later extending over the silicone debris on the surface (FIG. 9). To test the adhesive strength of the protein to the silicone, a simple scotch tape test was performed. The scotch tape could not be removed from the activated surface.

Adhesive Strength to the Retina

Figure 10:
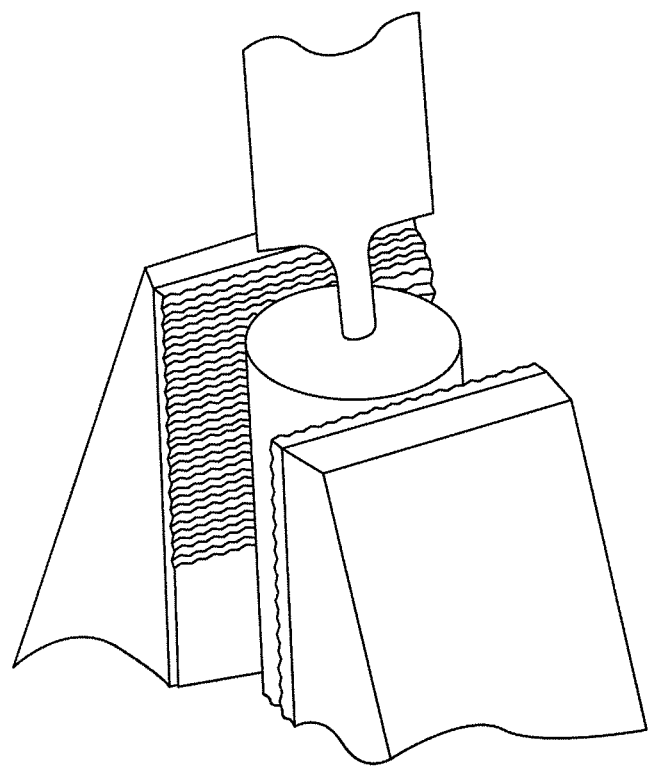
FIG. 10 is a photograph of a porcine retina being torn from its aluminum base by Contortrostatin coated silicone according to one embodiment of the invention.
Figure 11:
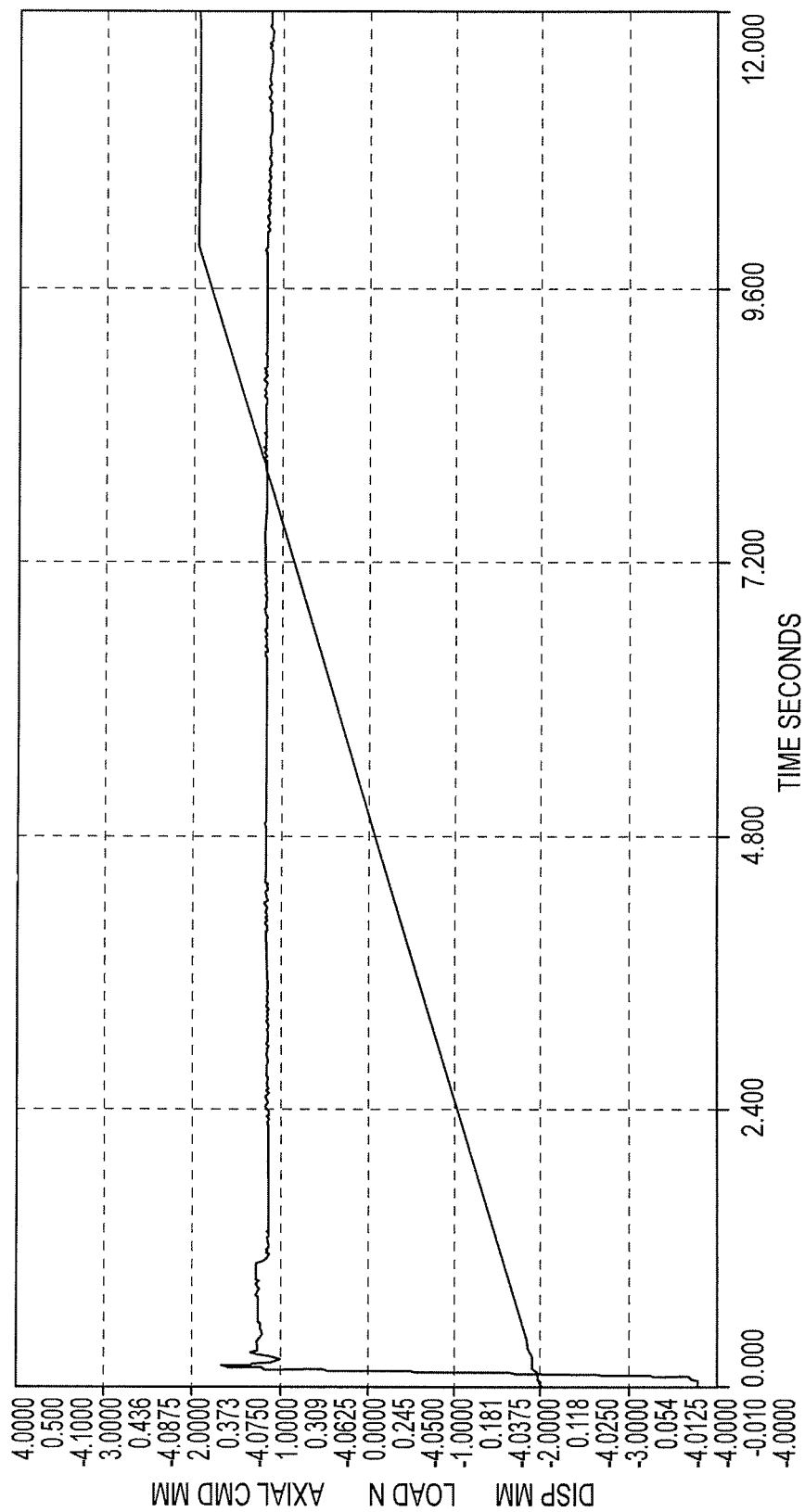
FIG. 11 is graph of the force needed to tear Contortrostatin coated silicone from an aluminum base.
Figure 12:
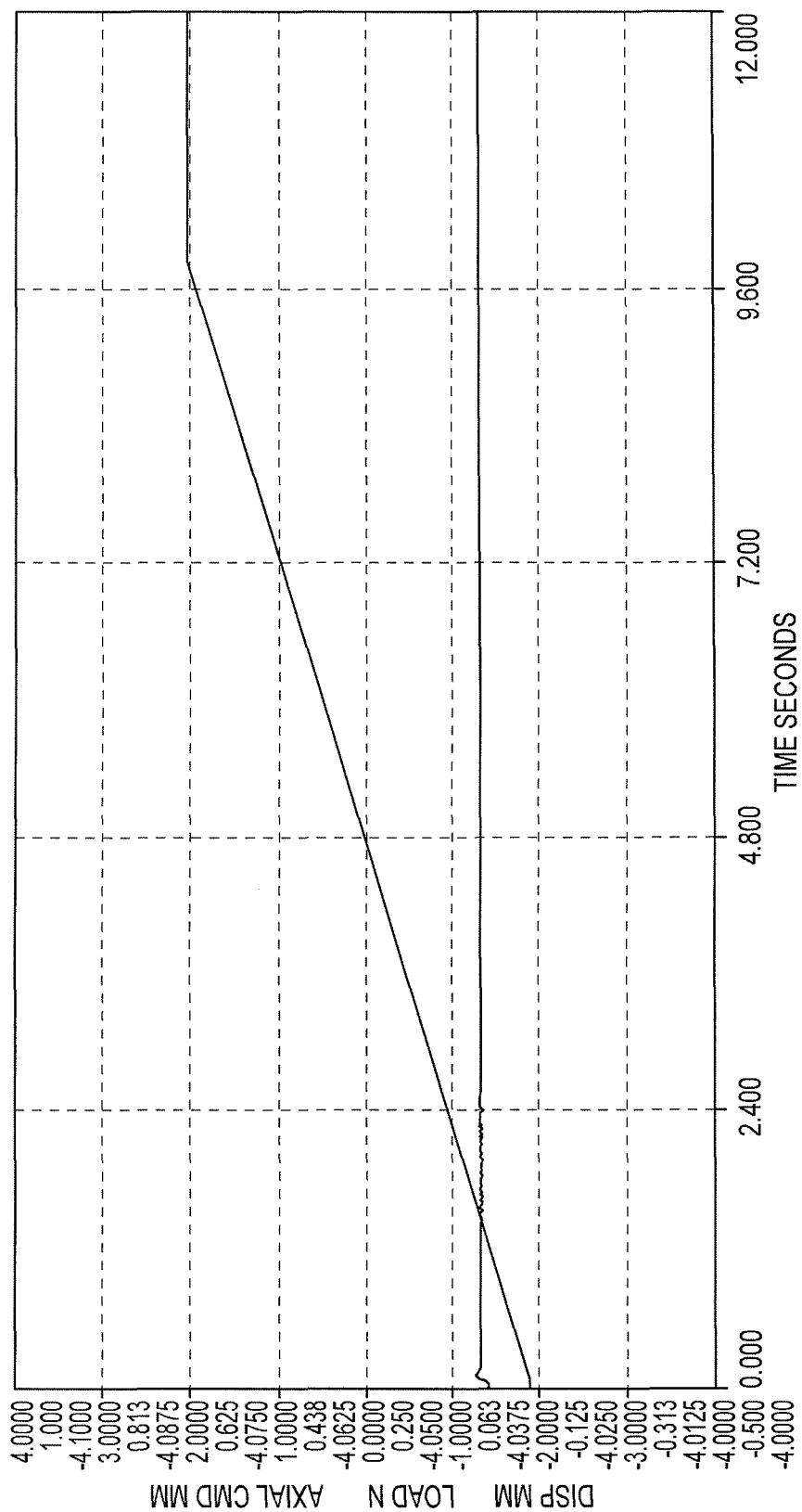
FIG. 12 is a graph of the force needed to tear uncoated silicone from an aluminum base.

Dynamic mechanical analysis of Contortrostatin-coated silicone and non-laser processed silicone is graphically presented in FIGS. 11 and 12. The silicone in each case was removed from the retina at 0.4 mm/second. FIG. 7 shows the adhesive force of the Contortrostatin-coated silicone is approximately 340 mN, at which point the retina was torn away from the aluminum surface (See Photo, FIG. 10). FIG. 12 shows the plain (non-activated) silicone is easily detached from retina after just 10 mN. The green line represents a force of 10 mN, and the blue line is a displacement of 4 mm over 10 seconds.

While this invention has been described in connection with reference to what are considered exemplary embodiments, the invention is not limited to the disclosed embodiments, dimensions, and configurations but, on the contrary, also extends to various modifications and equivalent arrangements. The invention is limited only by the appended claims and their equivalents.

What is claimed is:

1. A silicone article treated with a biocompatible compound that facilitates bonding to living tissue, comprising:
    a silicone substrate having (i) an original surface plane; (ii) an ablated and recessed first activated surface formed by irradiation with laser light at a wavelength and power sufficient to eject organic species from the silicone substrate by breaking Si—C bonds of the substrate below the original surface plane, the first activated surface being below the original surface plane; and (iii) an unrecessed second activated surface, adjacent the first surface, having thereon an adherent layer comprised of the ejected organic species; and
    at least one compound capable of binding to one or more integrins, coupled to the substrate.

2. A silicone article as recited in claim 1, wherein the compound capable of binding to one or more integrins comprises an arginine-glycine-aspartate (RGD) peptide, or a protein containing at least one RGD segment.

3. A silicone article as recited in claim 1, wherein the compound capable of binding to one or more integrins comprises an extracellular matrix (ECM) protein.

4. A silicone article as recited in claim 3, wherein the ECM protein is selected from the group consisting of fibronectin, laminin, and collagen.

5. A silicone article as recited in claim 1, wherein the compound capable of binding to one or more integrins comprises a non-ECM protein.

6. A silicone article as recited in claim 5, wherein the non-ECM protein comprises contortrostatin or vicrostatin.

7. A silicone article as recited in claim 1, wherein the article comprises or is part of an implantable medical device.

8. A silicone article as recited in claim 1, wherein the article is an epiretinal visual prosthesis.

9. A silicone article as recited in claim 1, wherein the wavelength and the power are selected such that the laser light preserves Si—O bonds in the substrate.

10. A silicone article as recited in claim 1, wherein the wavelength and the power are selected such that the laser light preserves Si—O bonds in the substrate.

11. A silicone article as recited in claim 1, wherein the recessed first activated surface is 10 microns or more below the original surface plane.

12. A biocompatible, implantable prosthesis, comprising:
    an implantable prosthesis partially or completely covered by a silicone having (i) an original surface plane; (ii) an ablated and recessed first activated surface having been irradiated with laser light at a wavelength and power sufficient to eject organic species from the silicone substrate by breaking Si—C bonds of the substrate below the original surface plane, the first activated surface being below the original surface plane; and (iii) an unrecessed second activated surface, adjacent the first surface, having thereon an adherent layer comprised of the ejected organic species; and
    at least one biocompatible compound capable of binding to one or more integrins, coupled to at least one activated surface.

13. A biocompatible, implantable prosthesis as recited in claim 12, wherein the implantable prosthesis comprises a microelectrode array.

14. A biocompatible, implantable prosthesis as recited in claim 12, wherein the biocompatible compound capable of binding to one or more integrins comprises an arginine-glycine-aspartate (RGD) peptide, or a protein containing at least one RGD segment.

15. A biocompatible, implantable prosthesis as recited in claim 14, wherein the compound capable of binding to one or more integrins comprises an extracellular matrix (ECM) protein.

16. A biocompatible, implantable prosthesis as recited in claim 15, wherein the ECM protein is selected from the group consisting of fibronectin, laminin, and collagen.

17. A biocompatible, implantable prosthesis as recited in claim 14, wherein the compound capable of binding to one or more integrins comprises a non-ECM protein.

18. A biocompatible, implantable prosthesis as recited in claim 17, wherein the non-ECM protein is selected from the group consisting of contortrostatin and vicrostatin.

19. A silicone article as recited in claim 12, wherein the wavelength and the power are selected such that the laser light preserves Si—O bonds in the substrate.

20. A silicone article as recited in claim 12, wherein the wavelength and the power are selected such that the laser light preserves Si—O bonds in the substrate.

21. A silicone article as recited in claim 12, wherein the recessed first activated surface is 10 microns or more below the original surface plane.

22. A method of making a biocompatible, implantable prosthesis, comprising:

providing an implantable prosthesis;

partially or completely covering the implantable prosthesis with a silicone having an original surface plane;

irradiating the silicone with laser light at a wavelength and power sufficient to eject organic species from the silicone by breaking Si—C bonds of the silicone below the original surface plane, thereby forming a recessed first activated surface beneath the original surface plane;

forming an adherent layer on an unrecessed second activated surface, adjacent the first activate surface, with the ejected organic species; and coupling at least one biocompatible compound capable of binding to one or more integrins to at least one activated surface.

23. A method as recited in claim 22, wherein the silicone coats the implantable prosthesis.

24. A method as recited in claim 22, wherein the silicone is provided as a jacket covering the implantable prosthesis.

25. A method as recited in claim 22, wherein the wavelength and the power are selected such that the laser light preserves Si—O bonds in the substrate.

26. A method as recited in claim 22, wherein the recessed first activated surface is 10 microns or more below the original surface plane.

* * * * *